US011953650B2

(12) United States Patent
Fujinaka

(10) Patent No.: US 11,953,650 B2
(45) Date of Patent: Apr. 9, 2024

(54) SHEET AND METHOD FOR PRODUCING SHEET

(71) Applicant: DAICEL-EVONIK LTD., Tokyo (JP)

(72) Inventor: Toshihiko Fujinaka, Tokyo (JP)

(73) Assignee: DAICEL-EVONIK LTD., Tokyo (JP)

( * ) Notice: Subject to any disclaimer, the term of this patent is extended or adjusted under 35 U.S.C. 154(b) by 638 days.

(21) Appl. No.: 16/972,353

(22) PCT Filed: May 31, 2019

(86) PCT No.: PCT/JP2019/021803
§ 371 (c)(1),
(2) Date: Dec. 4, 2020

(87) PCT Pub. No.: WO2019/235387
PCT Pub. Date: Dec. 12, 2019

(65) Prior Publication Data
US 2021/0231837 A1    Jul. 29, 2021

(30) Foreign Application Priority Data
Jun. 5, 2018 (JP) ................. 2018-108102

(51) Int. Cl.
| B29C 48/07 | (2019.01) |
| B29C 48/00 | (2019.01) |
| B29C 51/10 | (2006.01) |
| B29D 11/00 | (2006.01) |
| G02B 1/04 | (2006.01) |
| B29K 1/00 | (2006.01) |
| B29K 33/04 | (2006.01) |
| B29K 77/00 | (2006.01) |
| B29L 11/00 | (2006.01) |

(52) U.S. Cl.
CPC .......... *G02B 1/041* (2013.01); *B29C 48/0017* (2019.02); *B29C 48/07* (2019.02); *B29C 51/10* (2013.01); *B29D 11/00009* (2013.01); *B29K 2001/08* (2013.01); *B29K 2033/04* (2013.01); *B29K 2077/00* (2013.01); *B29K 2995/0026* (2013.01); *B29K 2995/0048* (2013.01); *B29L 2011/0016* (2013.01)

(58) Field of Classification Search
CPC ....... A61F 9/02; B29C 48/0017; B29C 48/07; B29C 51/10; B29C 48/022; B29C 48/08; B29C 48/131; B29D 11/00009; B29K 2001/00; B29K 2001/08; B29K 2033/04; B29K 2069/00; B29K 2077/00; B29K 2995/0026; B29K 2995/0048; B29L 2007/00; B29L 2011/0016; G02B 1/041; G02C 7/022
See application file for complete search history.

(56) References Cited

U.S. PATENT DOCUMENTS

| 5,177,910 A | * | 1/1993 | Norota ................ B24D 11/02 451/529 |
| 2002/0036359 A1 | | 3/2002 | Yamamoto et al. |
| 2007/0148462 A1 | | 6/2007 | Fujinaka et al. |
| 2011/0043902 A1 | | 2/2011 | Ishibashi et al. |
| 2016/0326289 A1 | | 11/2016 | Kitayama |

FOREIGN PATENT DOCUMENTS

| EP | 1 193 044 A2 | 4/2002 |
| EP | 1 804 088 A2 | 7/2007 |
| EP | 3 088 920 A1 | 11/2016 |
| JP | 5-50490 A | 3/1993 |
| JP | 6-166792 A | 6/1994 |
| JP | 9-5683 A | 1/1997 |
| JP | 9-85805 A | 3/1997 |
| JP | 2006-131789 A | 5/2006 |
| JP | 2006-224589 A | 8/2006 |
| JP | 2006-227591 A | 8/2006 |
| JP | 2008-274203 A | 11/2008 |
| JP | 2009-242752 A | 10/2009 |
| JP | 2010-37475 A | 2/2010 |
| TW | 201312166 A1 | 3/2013 |
| WO | WO 2012/102178 A1 | 8/2012 |

OTHER PUBLICATIONS https://chem.libretexts.org/Ancillary_Materials/Reference/Organic_Chemistry_Glossary/Alicyclic?readerView (Year: 2023).*
Chinese Office Action and Search Report for Chinese Application No. 201980037796.9, dated Feb. 9, 2023.
International Preliminary Report on Patentability and Written Opinion of the International Searching Authority for International Application No. PCT/JP2019/021803, dated Dec. 8, 2020, with an English translation.
International Search Report for International Application No. PCT/JP2019/021803, dated Aug. 13, 2019, with an English translation.
Chinese Office Action and Search Report for Chinese Application No. 201980037796.9, dated Mar. 15, 2022.
Japanese Office Action for Japanese Application No. 2018-108102, dated Mar. 1, 2022.
Extended European Search Report dated Jan. 20, 2022 for Application No. 19816077.2.

* cited by examiner

*Primary Examiner* — Lawrence D Ferguson
(74) *Attorney, Agent, or Firm* — Birch, Stewart, Kolasch & Birch, LLP

(57) ABSTRACT

The present invention provides a thin sheet with suppressed strain. The sheet according to the present invention has a thickness from 0.1 to 5 mm and is formed of a plastic that contains at least one resin selected from polyamide resins, polycarbonate resins, cellulose acrylate resins, and acrylic resins. A difference between a maximum value and a minimum value of retardation of the sheet is 3000 nm or less. The sheet according to the present invention can be obtained, for example, by subjecting a plastic containing at least one resin selected from polyamide resins, polycarbonate resins, cellulose acrylate resins, and acrylic resins to extrusion molding to obtain a plastic in the form of a sheet, and subjecting the resulting plastic in the form of a sheet to vacuum forming, air-pressure forming, or vacuum air-pressure forming.

13 Claims, No Drawings

SHEET AND METHOD FOR PRODUCING SHEET

TECHNICAL FIELD

The present invention relates to a sheet having low strain and a method for producing the sheet. The present application claims the priority to JP 2018-108102 filed in Japan on Jun. 5, 2018, the content of which is incorporated herein.

BACKGROUND ART

A plastic eyeglass lens or helmet shield is typically produced by subjecting plastic, which is a raw material, to injection molding, as described in Patent Document 1, for example. However, during injection molding, plastic flows through a narrow passage at high speed, and the resulting formed article tends to have a high strain. It is known that, in cases where a thin lens or shield is produced by injection molding, a particularly high strain remains. The problem was that a high strain in a lens or shield causes symptoms such as eye strain or headache, making it difficult to wear the lens or shield for a long period of time. In addition, a lens or a shield with high strain tended to crack easily when being processed. Therefore, there has been a need for a thinner lens or a thinner shield with suppressed strain.

CITATION LIST

Patent Document

Patent Document 1: JP 2010-37475 A

SUMMARY OF INVENTION

Technical Problem

Therefore, an object of the present invention is to provide a thin sheet having suppressed strain.

Another object of the present invention is to provide a lens or a shield having suppressed strain.

Yet another object of the present invention is to provide protective equipment including the sheet having suppressed strain.

Still another object of the present invention is to provide a method for producing a thin sheet having suppressed strain and a curved shape.

Solution to Problem

As a result of diligent research to solve the problems described above, the present inventors discovered that a thin sheet having suppressed strain can be obtained by subjecting a specific plastic to extrusion molding. The present invention was completed based on these findings.

That is, the present invention provides a sheet having a thickness from 0.1 to 5 mm and formed of a plastic containing at least one resin selected from polyamide resins, polycarbonate resins, cellulose acylate resins, and acrylic resins, wherein a difference between a maximum value and a minimum value of retardation of the sheet is 3000 nm or less.

The present invention also provides the sheet having a curved shape.

The present invention also provides the sheet having a haze value of 5% or less.

The present invention also provides the sheet in which the plastic has a photoelastic coefficient at 23° C. from $0.1 \times 10^{-12}$ to $100 \times 10^{-12}$ $cm^2/dyn$.

The present invention also provides the sheet in which the plastic contains an alicyclic polyamide resin.

The present invention also provides the sheet in which the alicyclic polyamide resin has a repeating unit represented by Formula (ad) below.

[Chem. 1]

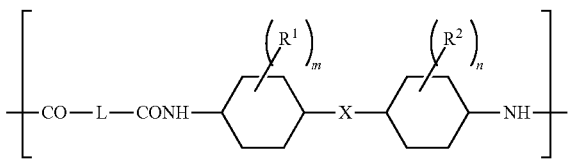

(ad)

where X is a single bond or a divalent hydrocarbon group, L is a divalent hydrocarbon group, $R^1$ and $R^2$ each is an alkyl group, and m and n each is an integer from 0 to 4.

The present invention also provides a lens including the sheet as a component.

The present invention also provides a shield including the sheet as a component.

The present invention also provides protective equipment having the lens or the shield including the sheet as a component.

The present invention also provides a method for producing the sheet having a curved shape by subjecting a plastic containing at least one resin selected from polyamide resins, polycarbonate resins, cellulose acylate resins, and acrylic resins to extrusion molding to obtain a plastic in the form of a sheet and subjecting the resulting plastic in the form of a sheet to vacuum forming, air-pressure forming, or vacuum air-pressure forming.

In the present specification, the retardation ($\Delta n \cdot d$) of a sheet is defined as a product of a birefringence ($\Delta n$) and a thickness (d).

Advantageous Effects of Invention

The sheet according to an embodiment of the present invention is thin and has low strain. In addition, the sheet has excellent transparency. Therefore, a lens or a shield made of the sheet according to an embodiment of the present invention provides excellent visibility, and by using this, problems such as eye strain or headache caused by the strain of the sheet can be resolved. The sheet is also lightweight. As a result, the sheet can be worn comfortably for a long period of time. Furthermore, the sheet has excellent processability, and when the sheet is being processed into eyeglasses, helmets, or the like, occurrence of cracking can be suppressed, improving the yield.

Especially, when the sheet according to an embodiment of the present invention is formed of a plastic containing a specific polyamide resin, the sheet is particularly light in weight, low in strain, less likely to crack even when a hole is directly formed on the sheet, and thus has excellent processability. The sheet also has excellent heat resistance and chemical resistance.

Thus, the sheet according to an embodiment of the present invention can be suitably used in eyeglasses such as sunglasses or goggles, helmets such as safety helmets, bike helmets, or sports helmets, medical face shields, face guards, and the like.

DESCRIPTION OF EMBODIMENTS

[Sheet]

A sheet according to an embodiment of the present invention is formed of a plastic containing at least one resin selected from polyamide resins, polycarbonate resins, cellulose acylate resins, and acrylic resins.

The thickness of the sheet according to an embodiment of the present invention is from 0.1 to 5 mm, and the upper limit is preferably 4 mm, and particularly preferably 2 mm. The lower limit is preferably 0.5 mm, and particularly preferably 1 mm.

The sheet according to an embodiment of the present invention has a small variation in retardation, and a difference between a maximum value and a minimum value of the retardation of the sheet, when in a size of 30 cm long and 30 cm wide, is 3000 nm or less, preferably 2000 mm or less, particularly preferably 800 mm or less, most preferably 500 nm or less, and particularly preferably 400 nm or less. Therefore, the sheet according to an embodiment of the present invention has low strain, and a lens or shield formed using the sheet according to an embodiment of the present invention can be worn comfortably for a long period of time without causing symptoms such as eye strain or headache.

In addition, the maximum value of the retardation of a sheet having a flat shape according to an embodiment of the present invention is, for example, 3000 nm or less, preferably 2500 nm or less, particularly preferably 1800 nm or less, most preferably 1000 nm or less, particularly preferably 500 nm or less, and most preferably 400 nm or less. The lower limit of the maximum value is, for example, 100 nm, and particularly 150 nm.

In addition, the minimum value of the retardation of the sheet having a flat shape according to an embodiment of the present invention is, for example, less than 100 nm, preferably 70 nm or less, particularly preferably less than 50 nm, and most preferably 45 nm or less. The lower limit of the minimum value is, for example, 10 nm, and particularly 5 nm.

The maximum value of the retardation of a sheet having a curved shape, for example, the shape of a lens with 6-base curvature, according to an embodiment of the present invention is, for example, 3000 nm or less, preferably 2500 nm or less, more preferably 2000 nm or less, particularly preferably 1000 nm or less, most preferably 600 nm or less, and most preferably 400 nm or less. The lower limit of the maximum value is, for example, 100 nm, particularly 150 nm, and further particularly 200 nm.

The minimum value of the retardation of the sheet having a curved shape according to an embodiment of the present invention is, for example, less than 100 nm, preferably 70 nm or less, particularly preferably less than 50 nm, and most preferably 45 nm or less. The lower limit of the minimum value is, for example, 10 nm, and particularly 5 nm.

The sheet according to an embodiment of the present invention may have a curved shape, for example, the shape of a lens or a shield. The sheet according to an embodiment of the present invention having a curved shape includes, for example, a lens with 4-base to 8-base curvature. The central thickness of the lens is, for example, from 0.5 to 2.5 mm, preferably from 1.0 to 2.0 mm, and particularly preferably from 1.5 to 2.0 mm.

The sheet according to an embodiment of the present invention has excellent transparency and a haze value of, for example, not greater than 5%, preferably not greater than 2%, particularly preferably not greater than 1%, and most preferably not greater than 0.9%. As a result, the sheet according to an embodiment of the present invention can be suitably used as a lens or a shield. The haze value in the present invention can be measured by a method according to JIS K 7136 (2000).

The photoelastic coefficient of the plastic forming the sheet according to an embodiment of the present invention at 23° C. is, for example, preferably from $0.1 \times 10^{-12}$ to $100 \times 10^{-12}$ cm$^2$/dyn, in that strain can be suppressed to a particularly low level, and more preferably from $0.1 \times 10^{-12}$ to $50 \times 10^{-12}$ cm$^2$/dyn, even more preferably from $0.1 \times 10^{-12}$ to $10 \times 10^{-12}$ cm$^2$/dyn, particularly preferably from $0.2 \times 10^{-12}$ to $7 \times 10^{-12}$ cm$^2$/dyn, and most preferably from $1 \times 10^{-12}$ to $5 \times 10^{-12}$ cm$^2$/dyn.

The sheet according to an embodiment of the present invention can be produced by subjecting a plastic containing at least one resin selected from polyamide resins, polycarbonate resins, cellulose acylate resins, and acrylic resins to extrusion molding.

Extrusion molding is a method in which a plastic that has been heated and melted in an extruder is discharged from a die and molded into a desired shape.

The heating and melting temperature can be appropriately selected depending on the plastic material, and is, for example, from 180 to 350° C., preferably from 200 to 330° C., and more preferably from 230 to 320° C.

The sheet having a curved shape according to an embodiment of the present invention can be produced by subjecting a plastic containing at least one resin selected from polyamide resins, polycarbonate resins, cellulose acylate resins, and acrylic resins to extrusion molding to obtain a plastic in the form of a sheet, or a sheet having a flat shape according an embodiment of the present invention, and in turn subjecting the resulting plastic in the form of a sheet to vacuum forming, air-pressure forming, or vacuum air-pressure forming.

The thickness of the plastic in the form of a sheet subjected to forming is preferably greater than the thickness of the desired formed article, for example, from above 1 time to 2 times the thickness of the desired formed article, and particularly preferably from 1.5 to 2 times the thickness of the desired formed article.

Vacuum forming is a method in which a plastic in the form of a sheet obtained through extrusion molding is heated and softened, guided onto a mold having the desired convex shape or concave shape or both, and sucked tightly onto the mold by a vacuum applied in the mold.

Air-pressure forming is the same method as vacuum forming except that the sheet is pressed tightly onto the mold by compressed air instead of vacuum suction.

Vacuum air-pressure forming is the same method as vacuum forming, except that the sheet is pressed tightly onto the mold by applying vacuum and compressed air simultaneously or at different times.

According to these methods, it is possible to suppress the residual stress inside the obtained sheet, and as a result, the occurrence of strain can be suppressed. In addition, a thinner sheet can be obtained compared to through injection molding or the like.

The plastic contains at least one resin selected from polyamide resins, polycarbonate resins, cellulose acylate resins, and acrylic resins described below. In addition, one or more additives selected from light modulating materials, light absorbers for ultraviolet light, blue light, infrared light, and the like, coloring agents, thermal stabilizers, light stabilizers, antioxidants, plasticizers, flame retardants, antistatic agents, and viscosity modifiers may be added within a range that does not impair optical properties or handling properties of the plastic, but the proportion of the resin, or the proportion of the total amount of resins when two or more resins are included, in the total amount of plastic (100 wt. %) is, for example, not less than 80 wt. %, preferably not less than 90 wt. %, and particularly preferably not less than 95 wt. %. The upper limit of the proportion of resin is 100 wt. %.

To obtain a thin sheet, or a lens or a shield, with strain suppressed to an extremely low level, the plastic preferably includes at least one resin selected from polyamide resins, cellulose acylate resins, and acrylic resins described below.

To obtain a thin sheet, or a lens or a shield, with strain suppressed to an extremely low level and excellent transparency, the plastic preferably includes at least one resin selected from cellulose acylate resins and acrylic resins described below.

To obtain a thin sheet, or a lens or a shield, that is lightweight and has strain suppressed to an extremely low level, excellent transparency, and great processability, the plastic preferably includes at least one resin selected from polyamide resins and polycarbonate resins described below, and in particular, the plastic preferably includes at least a polyamide resin.

Polyamide Resin

The polyamide resin is a polymer in which a multiple number of monomers are bonded through amide bonding, and examples include a polycondensation product of a diamine component and a dicarboxylic acid component as monomers and a ring-opening polymerization product of a lactam as a monomer. The diamine component and the dicarboxylic acid component each may be used alone, or in combination of two or more kinds. Furthermore, one kind of lactams, or a combination of two or more kinds of lactams may be used.

Examples of the diamine component include compounds represented by Formula (a) below.

[Chem. 2]

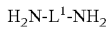

(a)

where $L^1$ is a divalent hydrocarbon group.

The divalent hydrocarbon group includes a divalent aliphatic hydrocarbon group, a divalent alicyclic hydrocarbon group, and a divalent aromatic hydrocarbon group.

Examples of the divalent aliphatic hydrocarbon group include linear or branched alkylene groups having from 1 to 20 carbons, such as a methylene group, a methylmethylene group, a dimethylmethylene group, an ethylene group, a propylene group, and a trimethylene group; linear or branched alkenylene groups having from 2 to 20 carbons, such as vinylene, 1-methylvinylene, propenylene, 1-butenylene, 2-butenylene, 1-pentenylene, and 2-pentenylene groups; and linear or branched alkynylene groups having from 2 to 20 carbons, such as ethynylene, propynylene, 3-methyl-1-propynylene, butynylene, 1,3-butadiynylene group, 2-pentynylene, 2-pentynylene, 2,4-pentadiynylene, 2-hexynylene, 1,3,5-hexatriynylene, 3-heptynylene, 4-octynylene, 4-nonynylene, 5-decynylene, 6-undecynylene, and 6-dodecynylene groups.

The divalent alicyclic hydrocarbon group is a group obtained by removing two hydrogen atoms from the structural formula of an alicycle, and examples of the alicycle include 3- to 20-membered cycloalkane rings, such as cyclopropane, cyclopentane, cyclohexane, cycloheptane, and cyclooctane rings; 3- to 20-membered cycloalkene rings, such as cyclopentene and cyclohexene rings; and bridged rings, such as perhydronaphthalene, norbornane, norbornene, adamantane, tricyclo[5.2.1.0$^{2,6}$]decane, and tetracyclo[4.4.0.1$^{2,5}$.1$^{7,10}$]dodecane rings. The alicycle may have a substituent (e.g., an alkyl group having from 1 to 5 carbons). Furthermore, two or more alicycles may be bonded through a single bond or a linking group (e.g., a divalent aliphatic hydrocarbon group).

The divalent aromatic hydrocarbon group is a group obtained by removing two hydrogen atoms from a structural formula of an aromatic ring, and examples of the aromatic ring include aromatic rings having from 6 to 20 carbons, such as benzene, naphthalene, anthracene, and fluorene rings. The aromatic ring may have a substituent (e.g., an alkyl group having from 1 to 5 carbons, a cycloalkyl group having from 3 to 6 carbons). Furthermore, two or more aromatic rings may be bonded through a single bond or a linking group (e.g., a divalent aliphatic hydrocarbon group or a divalent alicyclic hydrocarbon group).

Examples of the compound in which $L^1$ in Formula (a) above is a divalent aliphatic hydrocarbon group, that is, an aliphatic diamine, include hexamethylenediamine and trimethylhexamethylenediamine.

Examples of the compound in which $L^1$ in Formula (a) above is a divalent alicyclic hydrocarbon group, that is, an alicyclic diamine, include bis(p-aminocyclohexyl)methane and bis(4-amino-3-methylcyclohexyl)methane.

Examples of the compound in which $L^1$ in Formula (a) above is a divalent aromatic hydrocarbon group, that is, an aromatic diamine, include m-xylylenediamine.

Examples of the dicarboxylic acid component include compounds represented by Formula (c) below.

[Chem. 3]

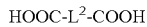

(c)

where $L^2$ is a divalent hydrocarbon group.

Examples of the divalent hydrocarbon group of $L^2$ include the same as those for the divalent hydrocarbon group of $L^1$.

Examples of the compound in which $L^2$ in Formula (c) above is a divalent aliphatic hydrocarbon group, that is, an aliphatic dicarboxylic acid, include adipic acid and dodecanedioic acid.

Examples of the compound in which $L^2$ in Formula (c) above is a divalent alicyclic hydrocarbon group, that is, an alicyclic dicarboxylic acid, include cyclohexane-1,4-dicarboxylic acid.

Examples of the compound in which $L^2$ in Formula (c) above is a divalent aromatic hydrocarbon group, that is, an aromatic dicarboxylic acid, include isophthalic acid and terephthalic acid.

Examples of the lactams include lactams having a 3 to 13-membered ring, such as α-lactam, β-lactam, γ-lactam, δ-lactam, ε-caprolactam, and ω-laurolactam.

According to an embodiment of the present invention, an alicyclic polyamide resin [that is, polycondensation product of a diamine component and a dicarboxylic acid component in which at least one of the diamine component or the dicarboxylic acid component is a compound having an alicyclic structure (e.g., an alicyclic diamine, an alicyclic dicarboxylic acid)] is preferred from the perspectives of excellent transparency, chemical resistance, impact resistance, oil resistance, and dimensional stability.

For the alicyclic polyamide resin, particularly a polycondensation product of an alicyclic diamine and an aliphatic dicarboxylic acid is preferred, and especially a polycondensation product having a repeating unit represented by Formula (ad) below is preferred.

[Chem. 4]

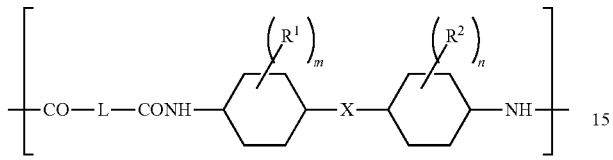

(ad)

where X is a single bond or a divalent hydrocarbon group, L is a divalent hydrocarbon group, $R^1$ and $R^2$ each is an alkyl group, and m and n each is an integer from 0 to 4.

Examples of the divalent hydrocarbon groups of X and L include the same as those for the divalent hydrocarbon group of $L^1$. X and L may be the same or different.

$R^1$ and $R^2$ each represent an alkyl group, and examples include linear or branched alkyl groups having from 1 to 5 carbons, such as methyl, ethyl, propyl, and isopropyl group. $R^1$ and $R^2$ may be the same or different. Furthermore, when m or n takes an integer of 2 or greater, two or more of the $R^1$ or $R^2$ may be the same or different. In an embodiment of the present invention, among these, both m and n are preferably zero.

The polyamide resin has a weight average molecular weight (calibrated with polystyrene), for example, from 6000 to 300000, and preferably from 20000 to 200000.

Furthermore, the polyamide resin may be crystalline or amorphous. Among these, from the perspective of excellent transparency, a polyamide resin with a low crystallinity, a microcrystalline polyamide resin having a crystal size that is smaller than the wavelength of light, or an amorphous polyamide (amorphous nylon or microcrystalline polyamide) is preferred.

The polyamide resin has a melting temperature of, for example, from 100 to 350° C., and preferably approximately from 100 to 320° C.

The polyamide resin typically has a high Abbe number, which is, for example, or greater, such as from 35 to 65, preferably 40 or greater, such as from 40 to 65, more preferably 45 or greater, such as from 40 to 60, and particularly preferably 50 or greater, such as from 50 to 60.

Furthermore, the polyamide resin has a refractive index of, for example, from 1.1 to 2.0, preferably from 1.2 to 1.9, and more preferably from 1.3 to 1.8.

A material with a high Abbe number tends to have a lower refractive index, but the polyamide resin has both a high Abbe number and a high refractive index, and thus has preferred optical functions in a well-balanced manner.

For the polyamide resin, for example, a commercially available product such as "Trogamid CX7323", available from Daicel-Evonik Ltd., and "Grilamid TR-90", available from EMS-CHEMIE (Japan) Ltd., can be suitably used.

A plastic made from the polyamide resin has a small photoelastic coefficient, and thus strain can be suppressed to an extremely low level. The plastic also has excellent heat resistance and chemical resistance. Furthermore, the plastic has a moderate hardness and excellent processability, and when the plastic is being processed into a piece of protective equipment, occurrence of cracking can be suppressed, improving the yield. The plastic made from the polyamide resin is also lightweight, and protective equipment using the plastic is light and can be comfortably worn over an extended period of time.

Polycarbonate Resin

The polycarbonate resin is a polymer having a repeating unit represented by Formula (d) below.

[Chem. 5]

(d)

where $L^3$ is a divalent hydrocarbon group.

$L^3$ is a divalent hydrocarbon group, and examples include the same as those for the divalent hydrocarbon group of $L^1$. $L^3$ is particularly preferably a divalent aromatic hydrocarbon group.

The polycarbonate resin can be produced, for example, by a transesterification process of a dihydroxy compound, preferably an aromatic dihydroxy compound, particularly preferably bisphenol A, and a carbonic acid diester, for example, diphenyl carbonate.

The polycarbonate resin has a weight average molecular weight (calibrated with polystyrene) of, for example, from 5000 to 300000, and preferably from 20000 to 200000.

A plastic made from the polycarbonate resin has excellent heat resistance and high hardness. Furthermore, the plastic has strong impact strength, and when the plastic is being processed into a piece of protective equipment, occurrence of cracking can be suppressed, improving the yield.

Cellulose Acylate Resin

The cellulose acylate resin is a polymer in which an acyl group is bonded to at least one of the carbon atoms in the 2-, 3-, and 6-positions of the β-1,4-linked glucose unit constituting the cellulose. In an embodiment of the present invention, the acyl group is preferably an acyl group having from 2 to 4 carbons, and particularly preferably contains at least an acetyl group. Therefore, when two or more types of acyl groups are contained, a combination of an acetyl group and a propionyl group or a butyryl group is preferable.

The total acyl substitution degree of the cellulose acylate resin is, for example, from 1.0 to 2.97, and within this range, from 2.0 to 2.9 is preferable from the perspective of excellent chemical resistance and processability.

Therefore, the cellulose acylate resin is preferably, for example, a cellulose acetate, such as cellulose diacetate or cellulose triacetate; and a cellulose acetate $C_{3-6}$ acylate, such as cellulose acetate propionate or cellulose acetate butyrate; among which cellulose triacetate is particularly preferable.

The cellulose acylate resin can be produced by acylating at least one of the hydroxyl groups bonded to carbon atoms in the 2-, 3-, and 6-positions of cellulose. Cotton linter or wood pulp such as hardwood pulp and softwood pulp can be used as the raw material of cellulose.

The cellulose acylate resin has a weight average molecular weight (calibrated with polystyrene), for example, from 50000 to 200000, and preferably from 60000 to 160000.

A plastic made from the cellulose acylate resin has a small photoelastic coefficient, and thus strain can be suppressed to an extremely low level. Furthermore, the plastic made from the cellulose acylate resin has excellent heat resistance and high hardness, and is lightweight. Therefore, protective equipment using the plastic made from the cellulose acylate resin is light and can be comfortably worn over an extended period of time.

Acrylic Resin

The acrylic resin is a polymer having a repeating unit represented by Formula (e) below. In addition to the repeating unit represented by Formula (e) below, the acrylic resin may also have other repeating units that can be copolymerized with the repeating unit represented by Formula (e) below.

[Chem. 6]

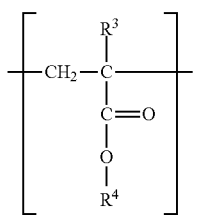

(e)

where $R^3$ is a hydrogen atom or a methyl group, and $R^4$ is a hydrogen atom or a monovalent hydrocarbon group.

Examples of the monovalent hydrocarbon group of $R^4$ include a monovalent group corresponding to the divalent hydrocarbon group of $L^1$.

Examples of the acrylic resin include homopolymers or copolymers of (meth)acrylic acid esters, (meth)acrylic-urethane copolymers (in particular, (meth)acrylic-urethane graft copolymers), styrene-(meth)acrylate copolymers, vinyl acetate-(meth)acrylate copolymers, ethylene-(meth)acrylate copolymers, ethylene-(meth)acrylic acid copolymers, (meth)acrylate-(meth)acrylic acid copolymers, styrene-acrylonitrile-(meth)acrylate copolymers, styrene-(meth)acrylate-(meth)acrylic acid copolymers, styrene-acrylonitrile-(meth)acrylate-(meth)acrylic acid copolymers, ethylene-vinyl acetate-(meth)acrylate copolymers, vinylpyrrolidone-(meth)acrylate copolymers, and styrene-butadiene-(meth) acrylic acid copolymers.

The acrylic resin has a weight average molecular weight (calibrated with polystyrene), for example, from 6000 to 500000, and preferably from 20000 to 350000.

A plastic made from the acrylic resin has a small photoelastic coefficient, and thus strain can be suppressed to an extremely low level. Furthermore, the plastic made from the acrylic resin has excellent heat resistance and high hardness, and is lightweight. Therefore, protective equipment using the plastic made from the acrylic resin is light and can be comfortably worn over an extended period of time.

Lens

The lens according to an embodiment of the present invention includes the sheet mentioned above as a component. Or, the lens according to an embodiment of the present invention is composed of the sheet, and in particular, the sheet having a curved shape. The lens according to an embodiment of the present invention may be composed of only the sheet mentioned above, or may include other components other than the sheet mentioned above. For example, one or more layers with a desired function, such as a hard coat layer, an anti-reflective layer, an anti-fog layer, an anti-smudge layer, a mirror layer, and other functional layer, may be laminated onto the surface of the sheet via an adhesion layer.

The adhesive forming the adhesion layer is not particularly limited as long as the sheet according to an embodiment of the present invention and the functional layer can be bonded with each other, and known adhesives, for example, acrylic adhesives, urethane adhesives such as ester polyurethane adhesives or ether polyurethane adhesives, epoxy adhesives, vinyl acetate adhesives, can be used. Among these, urethane adhesives are preferable from the perspective of excellent adhesive strength. For example, an urethane-based dry laminate adhesive formed from a combination of an ester-based polyurethane "TM-595" available from Toyo-Moton, Ltd. as a main agent, and a curing agent, such as curing agents under the trade names of "CAT-10L" and "CAT-RT85", both available from Toyo-Moton, Ltd., are commercially available.

An adhesive is preferably applied in such a manner that the thickness after curing is for example from 0.1 to 80 μm, preferably from 1 to 60 μm and particularly preferably from 5 to 40 μm.

The adhesive can be applied by, for example, printing methods and coating methods. Specific examples include methods such as screen printing methods, mask printing methods, offset printing methods, inkjet printing methods, flexographic printing methods, gravure printing methods, stamping, dispensing, squeegee printing methods, silk screen printing methods, spraying, and brushing.

The lens according to an embodiment of the present invention includes the sheet having a strain that is suppressed to an extremely low level as mentioned above, and thus is possible to suppress the occurrence of problems such as eye strain or headache. The lens is also lightweight. As a result, the lens can be worn comfortably for a long period of time.

Shield

The shield according to an embodiment of the present invention includes the sheet mentioned above as a component. Or, the shield according to an embodiment of the present invention is composed of the sheet, and in particular, the sheet having a curved shape. The shield according to an embodiment of the present invention may be composed of only the sheet mentioned above, or may include other components other than the sheet mentioned above. For example, one or more layers with a desired function, such as a hard coat layer, an anti-reflective layer, an anti-fog layer, an anti-smudge layer, a mirror layer, and other functional layer, may be laminated onto the surface of the sheet via an adhesion layer.

The shield according to an embodiment of the present invention includes the sheet having a strain that is suppressed to an extremely low level as mentioned above, and thus is possible to suppress the occurrence of problems such as eye strain or headache. The shield is also lightweight. As a result, the shield can be worn comfortably for a long period of time.

Protective Equipment

The protective equipment according to an embodiment of the present invention includes the above-mentioned lens or shield. Examples of the protective equipment according to an embodiment of the present invention include eyeglasses such as sunglasses or goggles, helmets such as safety helmets, bike helmets, or sports helmets, medical face shields, and face guards.

The protective equipment according to an embodiment of the present invention is lightweight and includes the above-mentioned lens or shield having a strain that is suppressed to an extremely low level, and thus is possible to suppress the occurrence of problems such as eye strain or headache, making it possible to comfortably wear the protective equipment for a long period of time.

EXAMPLE

Hereinafter, the present invention will be described more specifically with reference to examples, but the present invention is not limited by these examples.

Example 1

Extrusion Molding

A polyamide resin (available from Daicel-Evonik Ltd., trade name "TROGAMID CX7323", having an Abbe number of 45 and glass transition temperature of 140° C.) was heated and melted at 290° C. and then subjected to extrusion molding to obtain a plastic (1) in the form of a sheet with a length of 30 cm, a width of 30 cm, and a thickness of 2 mm.
Vacuum Forming The obtained plastic (1) in the form of a sheet was punched into a oval shape, having a major axis of 80 mm and a minor axis of 50 mm, using a Thomson blade and subjected to vacuum forming using a metal mold, having a mold temperature of 90° C. and cut into a shape of a lens with 6-base curvature, to obtain an eyeglass lens (1) with 6-base curvature having a center thickness of 1.9 mm.

Example 2

A plastic (2) in the form of a sheet with a thickness of 4 mm was obtained in the same manner as in Example 1 except that a polycarbonate resin (trade name "Iupilon", available from Mitsubishi Engineering-Plastics Corporation) was used instead of the polyamide resin.

Further, an eyeglass lens (2) having a thickness of 3.9 mm was obtained in the same manner as in Example 1 except that the plastic (2) in the form of a sheet was used instead of the plastic (1) in the form of a sheet.

Example 3

A plastic (3) in the form of a sheet with a thickness of 0.5 mm was obtained in the same manner as in Example 1 except that a triacetyl cellulose resin (trade name "Tenite", available from Eastman Chemical Company) was used instead of the polyamide resin.

Further, an eyeglass lens (3) having a thickness of 0.5 mm was obtained in the same manner as in Example 1 except that the plastic (3) in the form of a sheet was used instead of the plastic (1) in the form of a sheet.

Example 4

A plastic (4) in the form of a sheet with a thickness of 2 mm was obtained in the same manner as in Example 1 except that an acrylic resin (trade name "PARAPET", available from Kuraray Co., Ltd.) was used instead of the polyamide resin.

Further, an eyeglass lens (4) having a thickness of 1.8 mm was obtained in the same manner as in Example 1 except that the plastic (4) in the form of a sheet was used instead of the plastic (1) in the form of a sheet.

Comparative Example 1

A plastic (5) in the form of a sheet with a length of 30 cm, a width of 30 cm, and a thickness of 2 mm was obtained in the same manner as in Example 1 except that instead of extrusion molding, injection molding was performed using an injection molding machine available from FANUC Corporation at a resin temperature of 290° C. and a mold temperature of 90° C.

Comparative Example 2

An eyeglass lens (6) having a length of 6 cm, a width of 8 cm, and a thickness of 1.9 mm was obtained in the same manner as in Example 1 except that injection molding was performed instead of extrusion molding.

The retardation, haze value, and photoelastic coefficient of the sheet plastic obtained in the Examples and Comparative Examples were measured by the following methods.

Retardation: The retardation was measured using a retardation measurement device RETS-4200RV (available from Otsuka Electronics Co., Ltd.).

Haze value: The haze value was measured using a turbidity meter NDH 7000 (available from Nippon Denshoku Industries Co., Ltd.).

Photoelastic coefficient: The photoelastic coefficient was measured using a circular polarization measuring device KOBRA-WPR (available from Oji Scientific Instruments).

The retardation, haze value, and photoelastic coefficient of the eyeglass lens obtained in the Examples and Comparative Examples were measured by the same method as described above.

The results are summarized and shown in the table below.
[Table 1]

TABLE 1

|  |  |  | Example 1 | Example 2 | Example 3 | Example 4 | Comparative Example 1 | Comparative Example 2 |
|---|---|---|---|---|---|---|---|---|
| Sheet plastic | Retardation (nm) | Maximum value | 300 | 2000 | 200 | 300 | 5400 | — |
|  |  | Minimum value | 20 | 30 | 10 | 50 | 200 | — |
|  |  | Difference | 280 | 1970 | 190 | 250 | 5200 | — |
|  | Haze value (%) |  | 0.8 | 1.0 | 0.1 | 0.2 | 1.3 | — |
|  | Photoelastic coefficient at 23° C. ($cm^2/dyn$) |  | $4.0 \times 10^{-12}$ | $72 \times 10^{-12}$ | $2.0 \times 10^{-12}$ | $1.0 \times 10^{-12}$ | $4.0 \times 10^{-12}$ | — |
| Lens | Retardation (nm) | Maximum value | 350 | 2800 | 280 | 500 | — | 3300 |
|  |  | Minimum value | 20 | 50 | 10 | 50 | — | 100 |
|  |  | Difference | 330 | 2750 | 270 | 450 | — | 3200 |
|  | Haze value (%) |  | 1.0 | 1.2 | 0.3 | 0.3 | — | 1.0 |
|  | Photoelastic coefficient at 23° C. ($cm^2/dyn$) |  | $4.0 \times 10^{-12}$ | $72 \times 10^{-12}$ | $2.0 \times 10^{-12}$ | $1.0 \times 10^{-12}$ | — | $4.0 \times 10^{-12}$ |

To summarize the above, configurations and variations according to an embodiment of the present invention will be described below.

[1] A sheet having a thickness from 0.1 to 5 mm and is formed of a plastic containing at least one resin selected from polyamide resins, polycarbonate resins, cellulose acrylate resins, and acrylic resins, wherein a difference between a maximum value and a minimum value of retardation of the sheet is 3000 nm or less.

[2] The sheet according to [1], wherein the plastic contains at least one resin selected from polyamide resins, cellulose acylate resins, and acrylic resins.

[3] The sheet according to [1], wherein the plastic contains at least one resin selected from cellulose acylate resins and acrylic resins.

[4] The sheet according to [1], wherein the plastic contains at least one resin selected from polyamide resins and polycarbonate resins.

[5] The sheet according to any one of [1] to [4], wherein the total acyl substitution degree of the cellulose acylate resin is from 1.0 to 2.97, and preferably from 1.0 to 2.9.

[6] The sheet according to any one of [1] to [4], wherein the total acyl substitution degree of the cellulose acylate resin is from 1.0 to 2.97, and preferably from 2.0 to 2.97.

[7] The sheet according to any one of [1] to [6], wherein the cellulose acylate resin is a cellulose acetate C3-6 acylate.

[8] The sheet according to any one of [1] to [7], wherein the sheet has a curved shape.

[9] The sheet according to any one of [1] to [7], wherein the sheet is a lens having from 4-base to 8-base curvature.

[10] The sheet according to any one of [1] to [9], wherein a haze value is 5% or less.

[11] The sheet according to any one of [1] to [10], wherein a photoelastic coefficient of the plastic at 23° C. is from $0.1 \times 10^{-12}$ to $100 \times 10^{-12}$ cm$^2$/dyn.

[12] The sheet according to any one of [1] to [11], wherein the plastic is a plastic containing an alicyclic polyamide resin.

[13] The sheet according to [12], wherein the alicyclic polyamide resin has a repeating unit represented by Formula (ad).

[14] A lens including the sheet described in any one of [1] to [13] as a component.

[15] A shield including the sheet described in any one of [1] to [13] as a component.

[16] Protective equipment having the lens or the shield including the sheet described in any one of [1] to [13] as a component.

[17] A method for producing the sheet described in any one of [1] to [13] having a curved shape, wherein a plastic containing at least one resin selected from polyamide resins, polycarbonate resins, cellulose acylate resins, and acrylic resins is subjected to extrusion molding to obtain a plastic in the form of a sheet, and the resulting plastic in the form of a sheet is then subjected to vacuum forming, air-pressure forming, or vacuum air-pressure forming.

INDUSTRIAL APPLICABILITY

The sheet according to an embodiment of the present invention is thin and has low strain. In addition, the sheet has excellent transparency. The sheet is also lightweight. Furthermore, the sheet has excellent processability, and when the sheet is being processed into eyeglasses, helmets, or the like, occurrence of cracking can be suppressed, improving the yield. As a result, the sheet can be suitably used in eyeglasses, a shield of a helmet, a medical face shield, a face guard, or the like.

The invention claimed is:

1. A sheet having a thickness from 0.1 to 5 mm and comprising a plastic containing at least one resin selected from alicyclic polyamide resins, polycarbonate resins, cellulose acylate resins, and acrylic resins, wherein the alicyclic polyamide resin contains a repeating unit represented by the below Formula,

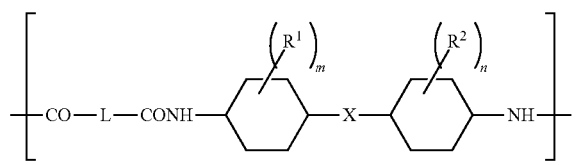

where X is a single bond or a divalent hydrocarbon group, L is a divalent hydrocarbon group, $R^1$ and $R^2$ each is an alkyl group, and m and n each is an integer from 0 to 4, and wherein a difference between a maximum value and a minimum value of retardation of the sheet is 3000 nm or less.

2. The sheet according to claim 1, wherein the sheet has a curved shape.

3. The sheet according to claim 1, wherein a haze value is 5% or less.

4. The sheet according to claim 1, wherein a photoelastic coefficient of the plastic at 23° C. is from $0.1 \times 10^{-12}$ to $100 \times 10^{-12}$ cm$^2$/dyn.

5. A transparent lens comprising the sheet described in claim 1 as a component, wherein said sheet and lens are both transparent.

6. A shield comprising the sheet described in claim 1 as a component.

7. Protective equipment comprising the lens or the shield including the sheet described in claim 1 as a component.

8. A method for producing the sheet described in claim 1 having a curved shape, wherein a plastic containing at least one resin selected from alicyclic polyamide resins, polycarbonate resins, cellulose acylate resins, and acrylic resins is subjected to extrusion molding to obtain a plastic in the form of a sheet, and the resulting plastic in the form of a sheet is then subjected to vacuum forming, air-pressure forming, or vacuum air-pressure forming, wherein the alicyclic polyamide resin contains a repeating unit represented by the below Formula,

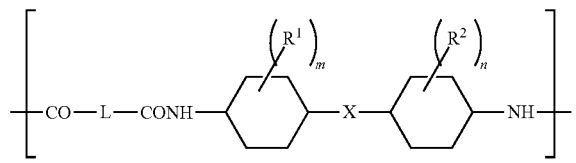

where X is a single bond or a divalent hydrocarbon group, L is a divalent hydrocarbon group, $R^1$ and $R^2$ each is an alkyl group, and m and n each is an integer from 0 to 4.

9. The sheet according to claim 1, wherein the plastic is a plastic containing alicyclic polyamide resins or cellulose acylate resins, wherein the alicyclic polyamide resin contains a repeating unit represented by the below Formula,

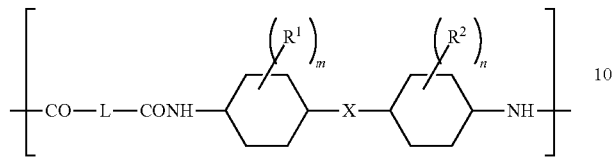

where X is a single bond or a divalent hydrocarbon group, L is a divalent hydrocarbon group, $R^1$ and $R^2$ each is an alkyl group, and m and n each is an integer from 0 to 4.

10. The sheet according to claim 1, wherein the plastic is a plastic containing cellulose acylate resins.

11. The sheet according to claim 1, wherein the plastic is a plastic containing cellulose acylate resins, wherein the total acyl substitution degree is from 1.0 to 2.97.

12. The sheet according to claim 1, wherein the maximum value of the retardation of a sheet is 2500 nm or less.

13. The sheet according to claim 1, wherein the minimum value of the retardation of a sheet is 50 nm or less.

* * * * *